US007983848B2

(12) United States Patent
Hoffman et al.

(10) Patent No.: US 7,983,848 B2
(45) Date of Patent: *Jul. 19, 2011

(54) COMPUTERIZED METHOD AND SYSTEM FOR INFERRING GENETIC FINDINGS FOR A PATIENT

(75) Inventors: Mark A. Hoffman, Lee's Summit, MO (US); David P. McCallie, Jr., Stilwell, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/751,292

(22) Filed: Jan. 2, 2004

(65) Prior Publication Data

US 2005/0075794 A1 Apr. 7, 2005

Related U.S. Application Data

(63) Continuation-in-part of application No. 09/981,248, filed on Oct. 16, 2001.

(60) Provisional application No. 60/509,023, filed on Oct. 6, 2003.

(51) Int. Cl.
*G01N 33/50* (2006.01)

(52) U.S. Cl. ............................ 702/19; 128/923; 600/300

(58) Field of Classification Search .................. None
See application file for complete search history.

(56) References Cited

U.S. PATENT DOCUMENTS

| 5,758,095 | A | 5/1998 | Albaum et al. |
| 5,833,599 | A | 11/1998 | Schrier et al. |
| 5,950,630 | A | 9/1999 | Portwood et al. |
| 5,985,670 | A | 11/1999 | Markin |
| 5,989,844 | A | 11/1999 | Shimada et al. |
| 6,067,524 | A | 5/2000 | Byerly et al. |
| 6,081,786 | A | 6/2000 | Barry et al. |
| 6,112,182 | A * | 8/2000 | Akers et al. ........................ 705/2 |
| 6,219,674 | B1 | 4/2001 | Classen |
| 6,315,720 | B1 | 11/2001 | Williams et al. |
| 6,931,326 | B1 | 8/2005 | Judson et al. |
| 7,509,263 | B1 | 3/2009 | Fiedotin et al. |
| 2002/0012921 | A1 | 1/2002 | Stanton, Jr. |
| 2002/0038227 | A1 | 3/2002 | Fey et al. |
| 2002/0046054 | A1 * | 4/2002 | Morand et al. ..................... 705/1 |
| 2002/0049772 | A1 | 4/2002 | Rienhoff, Jr. et al. |
| 2002/0052761 | A1 | 5/2002 | Fey et al. |
| 2002/0110823 | A1 | 8/2002 | Hogan |
| 2003/0011646 | A1 | 1/2003 | Levine et al. |
| 2003/0108938 | A1 * | 6/2003 | Pickar et al. ..................... 435/6 |
| 2003/0113727 | A1 | 6/2003 | Girn et al. |

FOREIGN PATENT DOCUMENTS

| EP | 1211627 A1 | 5/2002 |
| WO | WO 01/01218 * | 1/2001 |

OTHER PUBLICATIONS

Kobrinskii et al (Biomedical Engineering, vol. 31, No. 3, p. 172-174).*
Pathak et al (Proceedings of the Tenth Conference on Artificial Intelligence for Applications, p. 164-170, Mar. 1994).*
Coulson et al (Methods of Information in Medicine 2001; 40; 315-322.).*
Steadman's Medical Dictionary (entries for heredity and inheritance, p. 1-4, 2000).*
Yan et al. (Drug Information Journal, vol. 34, pp. 1247-1260, 2000).*
Roses (Nature, vol. 405, p. 857-865, Jun. 15, 2000).*
Wolf et al. (British Medical Bulletin, vol. 55, No. 2, p. 366-386, 1999).*
Wijker et al. (Hum. Mol. Gen., vol. 5, No. 1, p. 151-154, 1996).*
Lathrop et al. (PNAS, vol. 81, p. 3443-3446, 1984).*
Pratt et al. (Am. J. Hum. Genet., vol. 66, p. 1153-1157, 2000).*
Harris, N. L., "Probabilistic belief networks for genetic counseling" Computer Methods and Programs in Biomedicine, vol. 32 (1990) May, pp. 37-44.
Office Action issued in U.S. Appl. No. 09/981,248; Hoffman, et al.; Mar. 23, 2004.
Office Action issued in U.S. Appl. No. 09/981,248; Hoffman, et al.; Jul. 14, 2004.
Office Action issued in U.S. Appl. No. 09/981,248; Hoffman, et al.; Feb. 17, 2005.
Office Action issued in U.S. Appl. No. 09/981,248; Hoffman, et al.; Sep. 8, 2005.
Office Action issued in U.S. Appl. No. 09/981,248; Hoffman, et al.; Feb. 28, 2006.
Office Action issued in U.S. Appl. No. 10/826,595; Hoffman, et al.; Oct. 12, 2006.
Office Action issued in U.S. Appl. No. 10/826,595; Hoffman, et al.; Feb. 8, 2007.
Office Action issued in U.S. Appl. No. 10/826,595; Hoffman, et al.; Sep. 7, 2007.
Office Action issued in U.S. Appl. No. 10/826,563; Hoffman, et al.; Oct. 12, 2006.
Office Action issued in U.S. Appl. No. 10/826,563; Hoffman, et al.; Jan. 25, 2007.
Office Action issued in U.S. Appl. No. 10/826,563; Hoffman, et al.; Oct. 9, 2007.
Evans, William E., et al.,"Pharmacogenomi~s: Translating Functional Genomics into Rational Therapeutics," Science Magazine, vol. 286, No. 5439, Oct. 15, 1999, pp. 487-491.
Foubister, Yida, et al.,"Expanded Genetic Testing Carries New Legal Risks," American Medical News, Oct. 16, 1.

(Continued)

*Primary Examiner* — Karlheinz R Skowronek
(74) *Attorney, Agent, or Firm* — Shook Hardy & Bacon, LLP

(57) ABSTRACT

A method and system in a computing environment for inferring genetic findings for a patient is provided. The method includes receiving a request for genetic findings for a person from another application or a user. The method further includes inquiring as to whether the person has the genetic findings. If not, the method automatically provides inferred genetic findings for the person. The inferred genetic findings are calculated using genetic findings for family members of the patient, linkage analysis, haplotype analysis, semantic test results for the person and/or population genetics information.

21 Claims, 7 Drawing Sheets

OTHER PUBLICATIONS

Ichikawa, Y. Single nucleotide polymorphism to disclose severe side-effects or proper dosage for each patient. Internal Medicine. Jul. 2000. vol. 39, No. 7, pp. 523-524.

Lazarou, Jason, et al., "Incidence of Adverse Drug Reactions in Hospital Patients," JAMA, Apr. 15, 1998, vol. 279, No. 15.

Meyer, Un A.. et al., "Molecular Mechanisms of Genetic Polymorphisms of Drug Metabolism," Annu. Rev. Pharmacol, Toxicol. 1997, 37:269-96.

Sundberg, Magnus.Ingelman- et al., "Polymorphic Human Cytochrome P450 Enzyes: An Opportunity for Individualized Drug Treatment . . . ", J. Clin Pharmacol.2000; 40:930-938.

Usami et al.J. Human Genetics (1999) vol. 4415, pp. 304-307.

Office Action mailed Jun. 6, 2008 in U.S. Appl. No. 10/826,595, filed Apr. 16, 2005.

Office Action mailed Jul. 18, 2008 in U.S. Appl. No. 10/751,292, filed Jan. 2, 2004.

Office Action mailed Jul. 24, 2008 in U.S. Appl. No. 10/826,563, filed Apr. 16, 2004.

Office Action mailed Feb. 26, 2009 in U.S. Appl. No. 09/981,248, filed Oct. 16, 2001.

Office Action mailed Apr. 3, 2009 in U.S. Appl. No. 10/826,595, filed Apr. 16, 2004.

Office Action mailed Jul. 16, 2009 in U.S. Appl. No. 10/751,292, filed Jan. 2, 2004.

Office Action mailed Jul. 28, 2009 in U.S. Appl. No. 10/826,563, filed Apr. 16, 2004.

Office Action mailed Oct. 26, 2009 in U.S. Appl. No. 10/826,595, filed Apr. 16, 2004.

Office Action mailed Nov. 12, 2009 in U.S. Appl. No. 09/981,248, filed Oct. 16, 2001.

Office Action issued in U.S. Appl. No. 10/826,595; Hoffman, et al.; Jan. 27, 2007.

Office Action issued in U.S. Appl. No. 10/826,595; Hoffman, et al.; Sep. 7, 2007.

Office Action mailed Jun. 6, 2008 in U.S. Appl. No. 10/826,595.

Office Action mailed Jul. 24, 2008 in U.S. Appl. No. 10/826,563.

Office Action mailed Feb. 26, 2009 in U.S. Appl. No. 09/981,248.

Office Action mailed Apr. 3, 2009 in U.S. Appl. No. 10/826,595.

Office Action mailed Jul. 28, 2009 in U.S. Appl. No. 10/826,563.

Office Action mailed Oct. 26, 2009 in U.S. Appl. No. 10/826,595.

Office Action mailed Nov. 12, 2009 in U.S. Appl. No. 09/981,248.

Office Action mailed Jan. 21, 2010 in U.S. Appl. No. 10/826,563.

Office Action mailed Jun. 9, 2010 in U.S. Appl. No. 09/981,248.

Office Action mailed Jun. 14, 2010 in U.S. Appl. No. 10/826,595.

Office Action mailed Sep. 14, 2010 in U.S. Appl. No. 10/826,563.

* cited by examiner

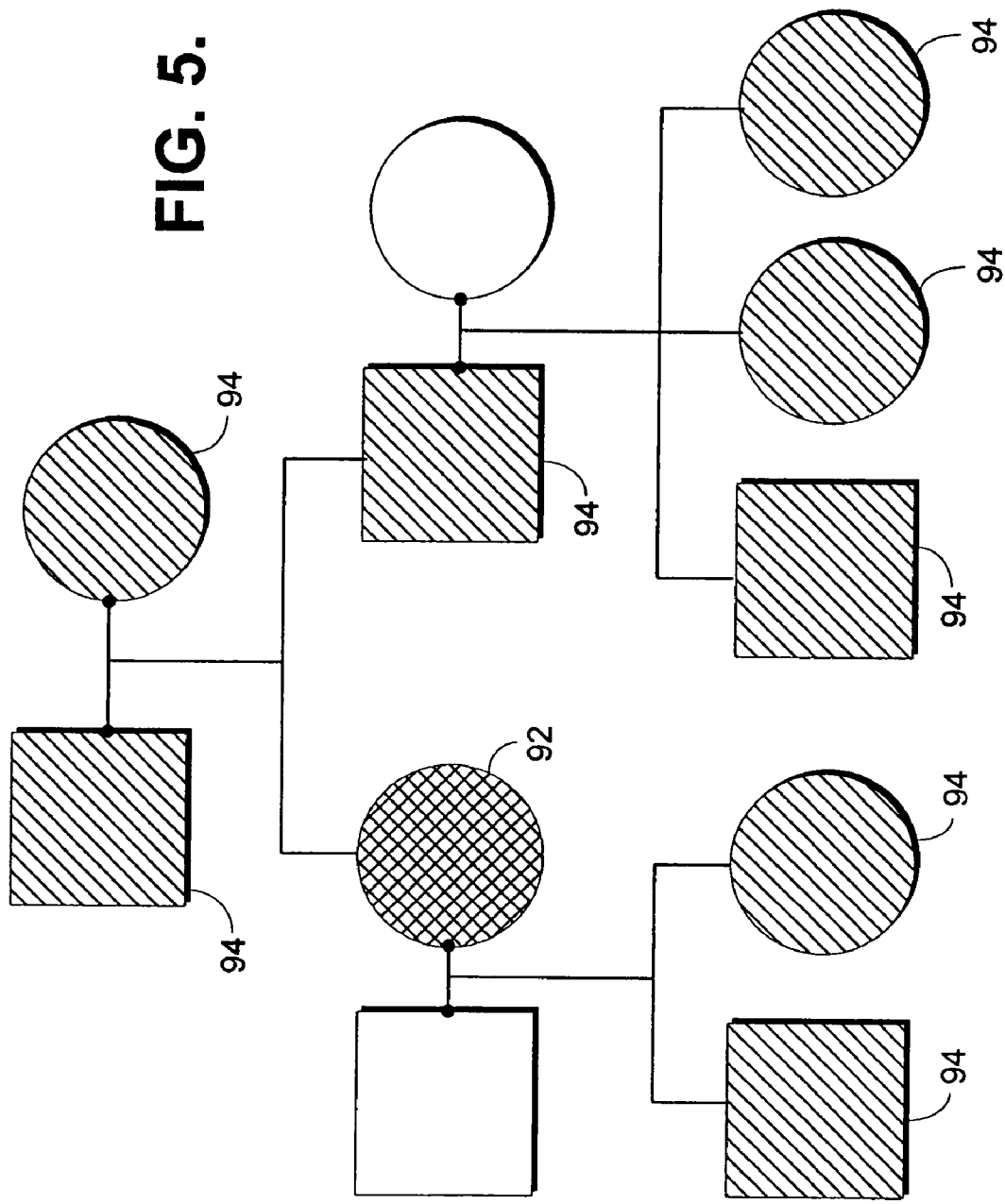

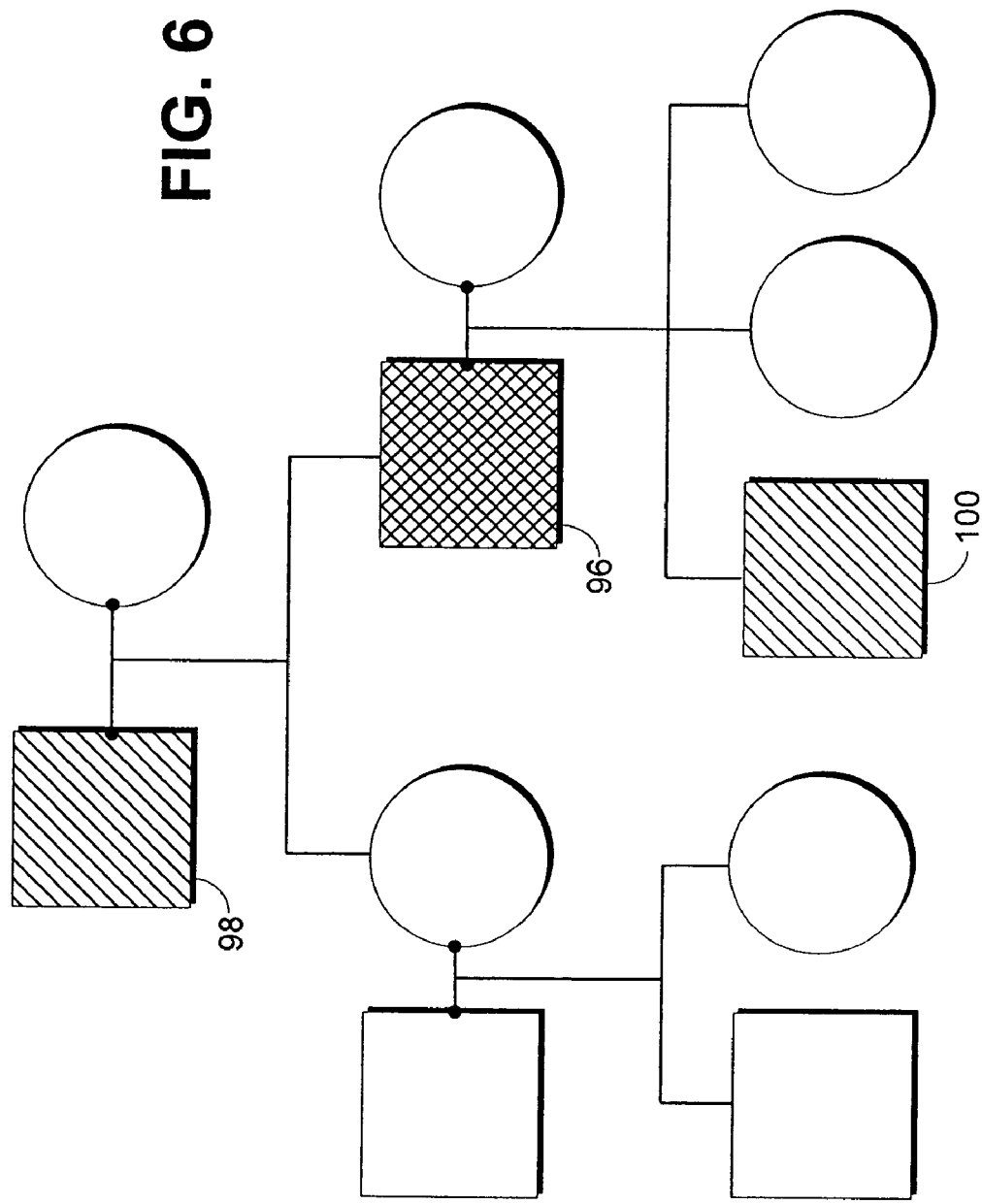

COMPUTERIZED METHOD AND SYSTEM FOR INFERRING GENETIC FINDINGS FOR A PATIENT

CROSS-REFERENCE TO RELATED APPLICATIONS

This application claims the benefit of priority of U.S. Provisional Application No. 60/509,023 filed on Oct. 6, 2003.

The present application is a continuation-in-part of co-pending U.S. application Ser. No. 09/981,248 filed Oct. 16, 2001, entitled COMPUTER SYSTEM FOR PROVIDING INFORMATION ABOUT THE RISK OF AN ATYPICAL CLINICAL EVENT BASED UPON GENETIC INFORMATION.

STATEMENT REGARDING FEDERALLY SPONSORED RESEARCH OR DEVELOPMENT

Not applicable.

TECHNICAL FIELD

The present invention relates generally to the field of computer software. More particularly, the invention relates to a method and system for inferring genetic findings for a patient.

BACKGROUND OF THE INVENTION

In recent years, genetic information has become increasingly available through research efforts such as the Human Genome Project. However, genetic information has not been incorporated effectively into the clinical decision making process. Genetic specialists have been among the first to incorporate this new information into their practice. However, non-specialists, such as general practitioners, pediatricians, surgeons and pharmacists, also need to improve their practices to reflect recent advances in genetics research even though they may lack a deep understanding of genetics.

As more genetic information has become available, technical advances have led to affordable genetic testing for many relevant genetic mutations. Nonetheless, most individuals have not undergone genetic testing and widespread use of genetic testing is likely to take five to ten years. Thus, for an individual patient, result values for mutations in a particular gene relevant to that patient's treatment may not always be available. However, genetic findings for one or more family members of the individual may be available. Demographic information and genetic findings for linked genes may also be available. While this information can be used to infer a genetic test result, it has not yet been integrated into an effective clinical process for the non-expert to use in the clinical decision making process.

Existing programs for inferring genetic finds are ineffective for a number of reasons. These programs require a user actively to solicit an inference. Once the user deliberately launches one of the existing programs, the program requires the user to complete a family tree by asking the user to indicate medical conditions known for each individual in the family tree. The user then selects an individual(s) in the family tree and the program returns a prediction. Thus, in these programs, the user must launch the program and specifically request a prediction for a particular person. Since the programs are not integrated into a unified healthcare information technology system, information about a person's family must be input manually. While the relationships are relatively simple, the genetic information is oftentimes difficult to understand and input into the system. As such, these programs are used by individuals with significant training and expertise in genetics. Even with skilled operators, the opportunities for human error are significant and the consequences of such errors is oftentimes great.

Accordingly, there is a need for an effective system and method for incorporating genetic information about the family of a patient into the clinical decision making process for the beneficial use by the non-expert. A need also exists for a system capable of inferring genetic findings for a patient when such a result would be useful in the decision making process but is absent for the patient being treated. Still another need is for a system that infers genetic findings for an individual in a reliable, cost effective, efficient and safe manner.

SUMMARY OF THE INVENTION

In one aspect of the present invention, a method and system in a computing environment for inferring one or more DNA test results for a person is provided. The system receives a query from another application seeking genetic findings for a person. The system inquires if the person has the genetic findings. If not, the system automatically provides inferred genetic findings for the person. Further, the system calculates the inferred genetic findings for the person. The system may calculate the inferred genetic findings based on the genetic findings of one or more family members of the person. Semantic test results for the person may be used to calculate inferred results for the person. The system may also calculate the inferred genetic findings using linkage analysis or haplotype analysis. Finally, the system may calculate the inferred genetic findings for the person by obtaining population genetic information for the person.

In another aspect, a method in a computer system for inferring DNA test results for a person is provided. A request from a user for actual genetic findings for one or more genes for a person is received. The method inquires whether the person has the genetic findings. If the person does not have the genetic findings, the method automatically provides inferred genetic findings for the person.

Further, the method calculates the inferred genetic findings for the person. The method may calculate the inferred genetic findings based on the genetic findings of one or more family members of the person. Semantic test results for the person may be used to calculate inferred results for the person. The method may also calculate the inferred genetic findings using linkage analysis or haplotype analysis. Finally, the method may calculate the inferred genetic findings for the person by obtaining population genetic information for the person

BRIEF DESCRIPTION OF THE SEVERAL VIEWS OF THE DRAWINGS

The present invention is described in detail below with reference to the attached drawing figures, wherein:

FIG. 5 is a diagram of an example of autosomal dominant inheritance; and

FIG. 6 is diagram of an example of a Y-linked inheritance.

DETAILED DESCRIPTION OF THE INVENTION

Figure 1:
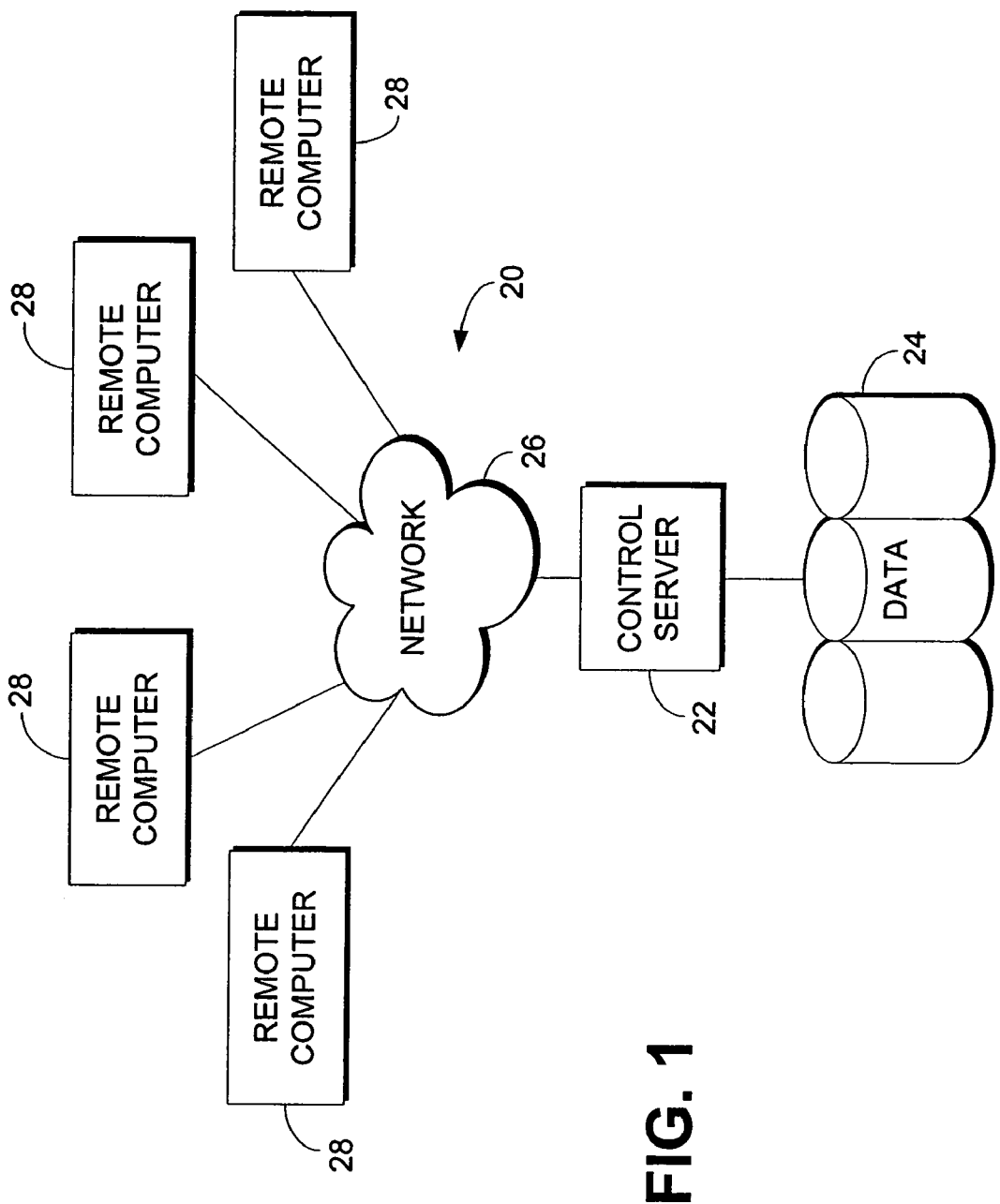
FIG. 1 is a block diagram of a computing system environment suitable for use in implementing the present invention.

The present invention provides a method and system capable of inferring genetic findings for a patient. FIG. 1 illustrates an example of a suitable medical information computing system environment 20 on which the invention may be implemented. The medical information computing system environment 20 is only one example of a suitable computing environment and is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include, but are not limited to, routines, programs, objects, components, data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical environment, for example, but not limited to, clinical laboratories, hospitals, other inpatient settings, a clinician's office, ambulatory settings, medical billing and financial offices, hospital administration, and home health care environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system operating in conjunction with an Internet based system, one skilled in the art would recognize that the method and system can be implement in any system supporting the receipt and processing of clinical agent information or genetic findings.

Figure 2A:
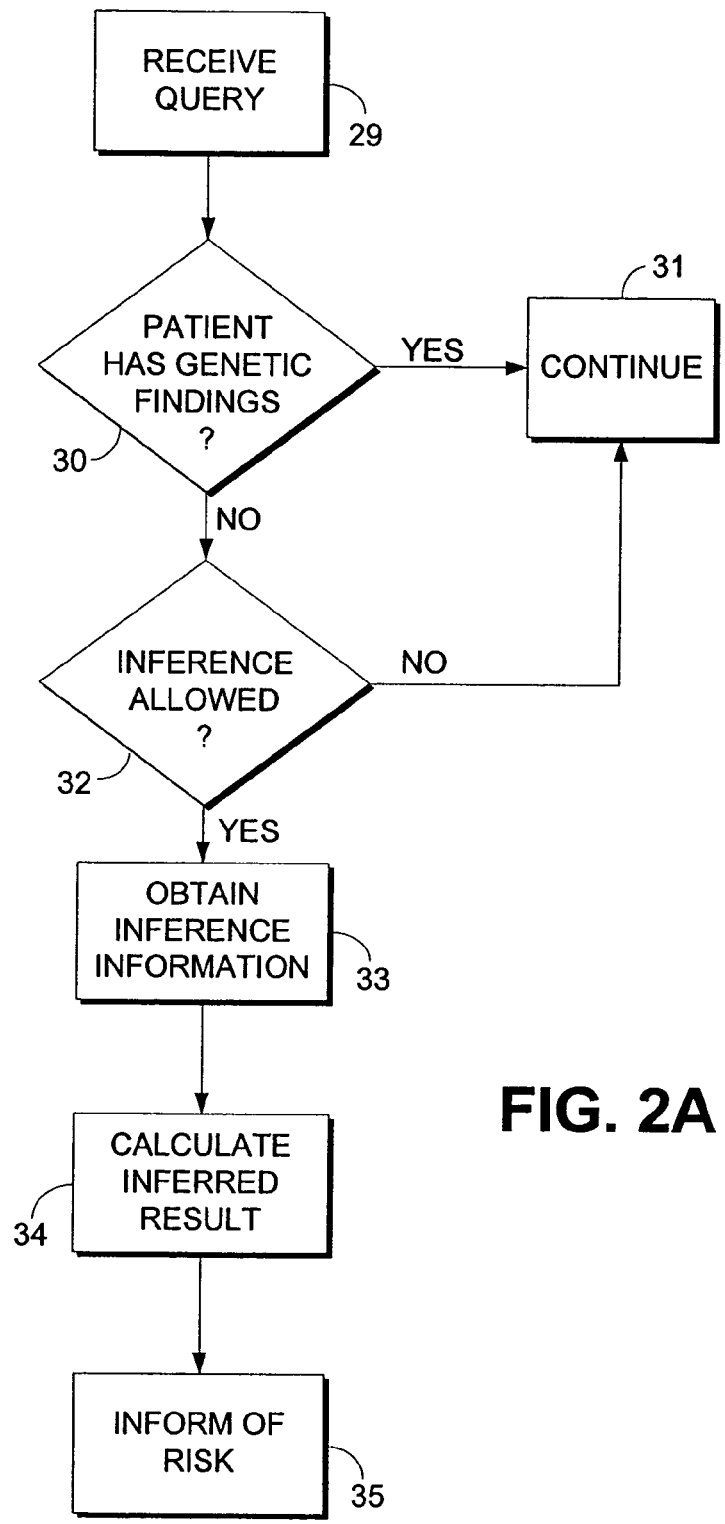
FIGS. 2A and 2B are flow diagrams of a method and system for inferring genetic findings in accordance with an embodiment of the present invention.

The system of the present invention uses genetics based logic without a user actively seeking to apply genetics to the clinical situation. In other words, the system provides a user with an unsolicited inference of genetic finding(s) for a person. With reference to FIG. 2A, in the first embodiment of the present invention, a system and method are provided for automatically inferring genetic findings for a person such as a patient. The system and method also utilizes inference information of a patient to infer genetic findings and the risk of an atypical clinical event (ACE).

Initially, at block 29, the system is queried. An application or module in a healthcare information technology (HCIT) system may query the system of the present invention for actual or inferred genetic findings for a patient. Alternatively, the system may receive a query directly from a user requesting actual genetic findings for a person. For example, when reviewing chest X-rays for a patient, a radiologist queries the system to determine if there are actual genetic findings for cystic fibrosis for the patient.

An example of a request embedded in an application is a request initiated by a decision support rule that queries for genetic findings. For instance, a computerized physician order entry (CPOE) application may have embedded logic to evaluate an electronic order to determine whether or not the order may be contraindicated and/or associated with particular genetic findings. The electronic order may be for a clinical agent, a clinical event or any of a number of orderables known to those of skill in the art. Clinical agents as used herein include drugs, pharmaceuticals, nutriceuticals, foods, salves, dietary supplements and the like. Clinical events include events such as lab tests, surgical procedures, therapies, orderable procedures, diagnoses, reflex, symptoms incoming results, scheduling events, documentation events, opening an electronic chart, registering a patient and combinations thereof.

In one embodiment, once an order is input or other action is taken within the HCIT system, a table or database is searched to determine if a clinical agent or event is associated with a genetic finding. The table includes a list of agents and events and any genetic findings that may be associated with each of the agents or events. As appreciated by those of skill in the art, a single agent or event may have associations with numerous genetic findings. Similarly, a genetic finding may have associations with more than one agent or event.

If the decision support rule determines that the clinical agent or event is contraindicated or otherwise associated with one or more genetic findings, the application queries the system of the present invention to check whether a patient has the genetic findings that may contraindicate or otherwise associated with the clinical agent or clinical event. One of skill in the art will appreciate that any variety of decision support rules and applications may query the system of the present invention. The system may also be queried by a user for actual genetic findings for the patient. For example, when reviewing chest X-rays for a patient, the radiologist queries the system to determine if there are actual genetic findings for cystic fibrosis for the patient.

At block 30, the system obtains information regarding whether the patient has genetic findings for which the query is directed. For example, the system may be queried to determine whether the patient has any genetic findings for a particular gene, such as the cystic fibrosis. The system may also be queried to find a specific genetic finding (e.g. a particular mutation in a specific gene.)

In one embodiment, the system would access the patient's electronic medical record to determine if the record contains the genetic findings. The genetic findings include genetic test results for any mutations of a particular gene, such as deletions, additions, insertions, inversions, duplications and complex rearrangements and any other type of mutations. Genetic findings may also include DNA sequence information, analysis of a polymorphic markers and phenotypic observations (such as blood type, PKU and other monogenetic traits with a well-understood basis).

In an alternative embodiment, a clinician checks to see if a patient has the genetic findings and enters a value(s) into the system to indicate the patient does or does not have genetic findings queried for. If the patient has the genetic findings, the system continues at block 31.

If the patient does not have the genetic findings, at block 32, the system determines whether inferred genetic findings for the patient are allowed. In one embodiment, the system searches an inference table, such as Table 1 below, to determine whether or not inferred results are allowed for the particular genetic findings. If inferred genetic findings are not allowed, the system continues at block 31. In one embodiment, block 32 is bypassed.

If inferred results are allowed, the system obtains inference information at block 33. The inference information can include genetic information of family members, genetic findings for linked genes or markers, semantic information, population genetics information or combinations thereof.

At block 34, the system utilizes the inference information to calculate inferred genetic findings for the patient. The system can calculate the inference in any variety of ways. For instance, the system could infer genetic findings for a patient based on the genetic findings for members of the patient's family. The system utilizes genetic inheritance principles to calculate inferred genetic findings for a patient using genetic findings for the patient's family members.

The system can calculate an inference based on information embedded in a semantic network describing biological information. For example, the system utilizes cytogenetic observations for the patient, such as the absence of a chromosomal band, to calculate an inferred result. For example, cytogenetic testing reveals that a patient has a deletion in chromosome 4 that includes band 4q12.1. Based on this information, the system can infer that the patient is likely to missing one copy of gene A, described by the semantic network as being included in band 4q12.1.

The system may also calculate an inference using linkage analysis. Linkage analysis uses genetic maps that show the physical location of genes and markers related to one another. It is known that genes and markers located on the same chromosome and which are close to one another are likely to be co-inherited. Knowledge of the genotype of one or more genes or genetic markers may also be used to make a reasonable estimation of the genotype of an adjacent gene when given the genotype using statistical algorithms and haplotype maps. This inference calculation utilizes genetic findings for members of the patient's family, genetic findings for any linked genes or markers for members of the patient's family and genetic findings for any linked genes or markers for the patient.

The system may also infer results based upon genetic findings for any linked genes or markers for the patient. In other words, the system may perform a haplotype analysis for the patient and calculate inferred genetic findings. To perform a haplotype analysis, genetic maps showing the physical location of genes and markers related to one another and statistical algorithms are used. For example, relative to three genes arranged linearly on a chromosome (A, B and C), a haplotype map might indicate a person who has version 1 of gene A and version 2 of gene B is 90% likely to have version 2 of gene C. On the other hand, the general population is only 2% likely to have version 2 of gene C.

The system may also calculate inferred genetic findings based on population genetics information. The system of the present invention may use any combination of inference information to calculate an inference of genetic findings for a patient.

At block 35, the system informs the user of the inferred genetic findings. The system may also inform whether the inferred genetic findings indicate a high risk of an atypical event. An atypical event as used herein includes (a) adverse reactions to a clinical agent or clinical event and (b) reactions to the clinical agent or event that result in little or no benefit to the patient. If the system determines that there is little likelihood the patient has the genetic findings associated with an atypical event, the system can continue without notifying the clinician of the inferred genetic finding and/or the risk. On the other hand, the system can communicate the inferred genetic finding and/or any associated risks to the clinician. Alternatively, if the system determines there is a high likelihood that the patient has the genetic finding associated with an atypical event, the system may send a message to the user or clinician informing them of the inferred result at block at block 35.

The message can be communicated by a graphical display window indicating the probability that the patient may experience an atypical event. The message also may be communicated by alphanumeric page, e-mail or any other form of automated communication.

Additional clinical action may be taken based on the inferred result determined by the system. For example, the inferred result may be recorded in a central medical system into the patient's electronic medical record, a confirmatory genetic test may be ordered for the patient, the administration of the clinical action may be delayed or canceled, additional therapy scheduled, an alternative agent may be selected, or the patient may be referred to a clinical counselor. Procedures may also be ordered for the patients based in the inferred genetic finding. For instance, if the system has determined that a patient is 50% likely to have the mutant version of the BRCA1 gene that increases her risk of developing breast cancer, mammograms may be scheduled for the patient on a biyearly basis, rather than a yearly basis, based on the inferred genetic finding.

Figure 2B:
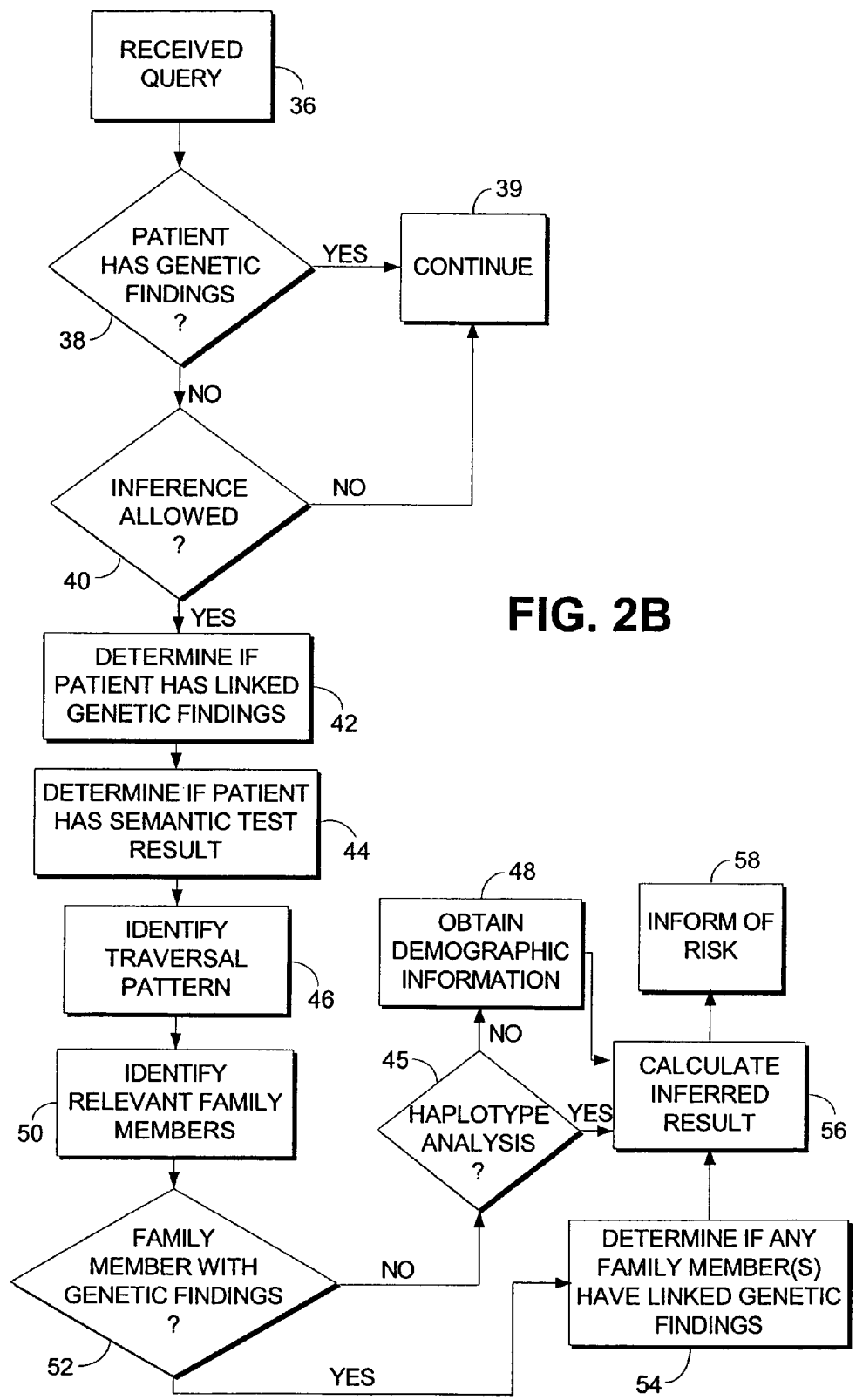

With reference to FIG. 2B, another system and method are provided for inferring genetic findings for a patient is provided. At block 36, the system is queried. The system may be queried by another application for actual or inferred genetic findings for a particular patient. Alternatively, a user may directly query the system for actual genetic findings. At block 38, the system determines whether the patient has the genetic finding. If the patient has the genetic finding, the system continues at block 39. If the patient does not have the genetic finding, at block 40, the system determines whether inferred genetic findings are allowed.

If inferred genetic findings are allowed, at block 42, the system determines whether the patient has genetic findings for any genes or genetic markers linked to genetic findings for which the query is directed. In one embodiment, the system searches an inference table to determine the maximum distance to search for related results or "Max LOD". Table 1 is an example of a portion of an inference table.

| Gene | Mode of Inheritance | Chromo-somal Location | Max LOD | Inference Allowed | Number of Generations |
| --- | --- | --- | --- | --- | --- |
| CYP2D6 | Autosomal | | | Yes | 2 |
| RYR1 | Autosomal | 19q13.1 | 100 cM | No | 0 |
| CBP | X linked | X28 | 50 cM | Yes | 3 |

For example, if system has been queried to find any genetic findings for the RYR1 gene, the system will search for genetic findings for linked genes or markers within 100 centimorgans from chromosome 19, arm q band 13. Preferably, the system accesses a database containing personal information about the patient to obtain genetic findings for linked genes or genetic markers. The system may also include a database representing the genomic positions of genes and markers in order to support these calculations. If the system obtains genetic findings for linked genes or genetic markers, the system can utilize this information to perform a linkage analysis or haplotype analysis to calculate inferred genetic findings for the patient as described below. In one embodiment, block 42 is bypassed.

At block 44, the system determines if the patient has semantic test results for the genetic findings for the patient. If so, the system may utilize this factor to calculated inferred genetic findings or may use the semantic test results with other inference information to calculate an inferred genetic finding for the patient. In one embodiment, block 44 is bypassed.

Figure 3:
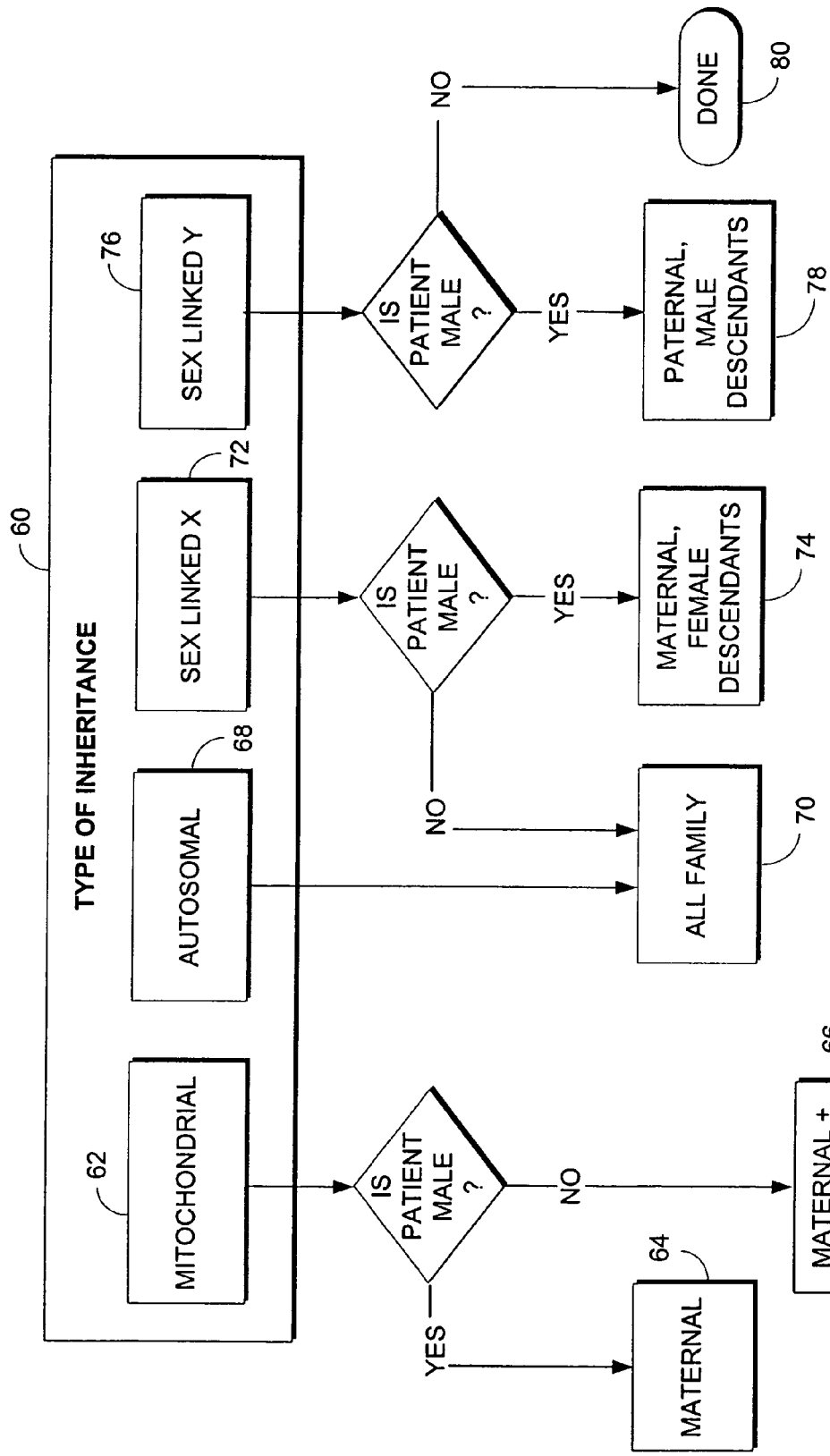
FIG. 3 is a diagram illustrating examples of modes of inheritance.
Figure 4:
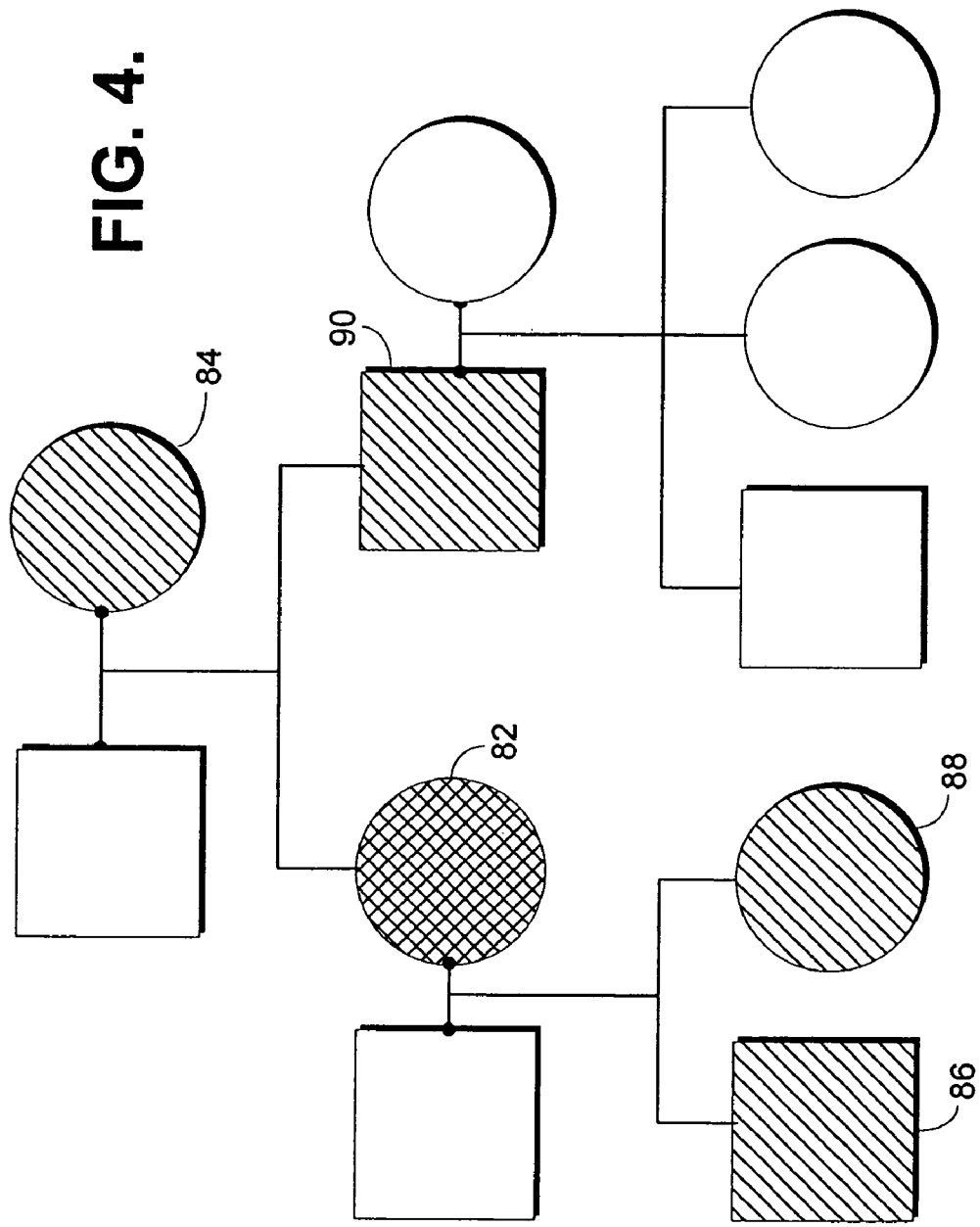
FIG. 4 is a diagram of an example of mitochondrial inheritance.

Next at block 46, the system identifies the appropriate traversal pattern for the genetic findings for which the query is directed. In one embodiment, the system searches an inference table to obtain the mode of inheritance for the genetic findings as shown above in Table 1. Based on the mode of inheritance, the system determines which family members are within the traversal pattern and should be examined. With reference to FIG. 3, four modes of inheritance 60 are illustrated. A mitochondrial DNA mode of inheritance 62 leads to a traversal in which the female ancestors of the family and their progeny and all progeny 64 of a female patient are examined. For male patients, only the female ancestors and the female ancestors' progeny 66 are examined. As can be seen in FIG. 4, the female ancestors 84 of the female patient 82 and the ancestors' progeny 82, 90 and the progeny of the female patient 86, 88 are examined.

With reference back to FIG. 3, an autosomal mode of inheritance 68 obeys classical Mendelian inheritance and requests a traversal of all blood relatives 70. As can be seen in FIG. 5, all blood relatives 94 of the patient 92 are examined.

With reference to FIG. 3, an X linked mode of inheritance 72 leads to a traversal in which female ancestors and all offspring of a male patient are examined. For a female patient, all female ancestors and their maternal descendents and all descendants of the female patient 74 are examined.

A Y linked mode of inheritance 76 leads to a traversal in which only male relatives or descendants of a male patient 78 are examined. If the patient is female, no family or descendants 80 are examined. As can be seen in FIG. 6, all male ancestors 98 of the male patient 96 and male progeny 100 of a male patient 96 are examined.

Referring again to FIG. 2B, at block 50, the system identifies family member(s) of the patient who fall within the traversal pattern. In one embodiment, a database having documentation of family relationships is accessed. The number of generations of family members who are examined may be limited. In one embodiment, the system searches an inference table, such as Table 1, to determine the maximum number of generations of family members who are examined for genetic findings.

At decision block 52, the system determines whether the family member(s) within the traversal pattern have the genetic findings. For example, the system obtains from a database the medical records of each family member who qualifies for the traversal. The medical records are checked to determine whether or not the family member has the genetic findings.

If at decision block 52 the system determines that no family members within the traversal pattern have the genetic findings, at block 45, the system determines if the patient had genetic findings for any linked genes or markers and if so performs a haplotype analysis at block 56. As discussed above, a haplotype analysis uses maps and statistical algorithms to predict the most likely variant for the genetic finding being queried for.

If at block 45, the patient does not have genetic findings for any linked genes the system obtains demographic information for the patient at block 48. At block 56 the system utilizes the demographic information to calculate a population genetics inference. As known in the art and as set forth in the example that follows, gender, ethnic, and geographic distribution information is indicative of genetic predisposition to certain conditions. For instance, numerous studies have found that the frequency of mutations in drug acetylation may vary among populations of different ethnicity and geographic origin. Meyer et al., *Molecular Mechanisms of Genetic Polymorphisms of Drug Metabolism,* Annu. Rev. Pharmacol. Toxicol., 1997: 37: 269-295. By way of example, 40-70% of those in populations of European and North American descent display acetylators of izoniazid, compared to only 10-30% of those from Pacific Asian populations. Other genes have widely varying genotypic frequencies. For example, mutated forms (or alleles) of one particular gene, CYP2D6, vary greatly between Caucasian, Asian, Black African, and Ethiopian and Saudi Arabian populations. Ingelman-Sundberg et al, *Polymorphic human cytochrome P450 enzymes: an opportunity for individualized drug treatment,* Trends. Pharmacol. Sci., 1999: 20(8):342-349.

If at decision block 52, the system determines there are one or more family member(s) of the patient who have the genetic findings, the system determines whether those family member(s) also have genetic findings for linked genes or markers at block 54. In one embodiment, block 54 is bypassed.

Next at block 56, the system calculates an inferred result for the patient. The inferred results are calculated using the genetic findings for family member(s). The system uses Pro Form a logic, Bayesian calculations or other statistical or algorithmic approaches to infer results for the patient. The system utilizes the familial genetic findings to infer a genetic finding for the patient.

The system may also calculate the likelihood the patient has a gene variant indicative of an atypical event based on the inferred genetic finding. In one embodiment, the system searches the polymorphism/risk table or database for the inferred genetic finding and determines if there are any risks associated with the inferred genetic finding.

The system performs a linkage analysis using genetic maps that show the physical location of genes relative to one another and statistical algorithms. As discussed above, it is known that genes or markers located on the same chromosome and are close to one another are likely to be co-inherited.

In this embodiment, the inferred results are calculated by utilizing genetic findings for linked genes or markers for the patient, genetic findings for linked genes or markers for one or more family members, and the genetic findings for one or more family members. Linkage analysis may be performed using Quantitative Trait Loci (QTL) analysis or any other approach known to those skilled in the art.

At block 58, the system informs the user of the inferred genetic finding. Again, the system may also inform whether the inferred result indicates a high risk of an atypical event. If the system determines there is a high likelihood that the patient has the genetic findings associated with an atypical event, the system may send a message to the user or clinician informing them of the inferred result at block at block 58. The message can be communicated by a graphical display window indicating the probability that the patient may experience an atypical event. The message also may be communicated by alphanumeric page, e-mail or any other form of automated communication. This message can also provide the user with information about the mode of inference that was applied.

Additional clinical action may be taken based on the inferred result determined by the system. For example, the inferred result may be recorded in a central medical system by appending the result into the patient's electronic medical record, a confirmatory genetic test may be ordered for the patient, the administration of the clinical action may be delayed or canceled, additional therapy scheduled, an alternative agent may be selected, or the patient may be referred to a clinical counselor.

In operation, by way of example, a child is seriously injured while playing at a friend's home. He is rushed to the local emergency room. During the preparations for surgery, the attending surgeon chooses a protocol that would involve the use of halothane. A decision support rule determines that a mutation in the RYR1 gene can lead to malignant hyperthemia in response to halothane. With reference to FIG. 2B at block 36, the system is queried for an actual genetic finding for the RYR1 gene for the patient. At block 38, the system determines that the patient does not have any genetic findings for the RYR1 gene. Blocks 40, 42 and 44 are bypassed. At block 46, the system determines that the traversal pattern for the gene is autosomal dominant and at block 52 the system searches to determine whether any of the patient's family had been tested for this trait. The system determines at block 52 that the child's father had been tested and found to have a mutation in the RYR1 gene. Block 54 is bypassed. At block 56, the system calculates an inferred genetic finding for the patient and determines that there is a 50% chance that the child has the mutated gene that leads to malignant hyperthemia in response to halothane. At block 58, the system informs of the risk by notifying the surgeon with a page of the inferred result and warning her that there is a 50% chance that child would have a severe reaction to halothane. In response to the information, the surgeon chooses an alternative protocol and the child recovers fully from his injury. Subsequently, a follow-up genetic test is ordered to confirm whether or not the child is actually at risk.

In a second example, a woman is seen by her gynecologist and requests estrogen therapy as a means to help her with menopause. A decision support rule determines that a mutation in the Factor V gene in combination estrogen therapy increases the risk of thrombosis and queries the system at block 36 for actual genetic findings for the Factor V gene for the patient. At decision block 38, the system determines the patient does not have genetic findings for the Factor V gene. Block 40 is bypassed. However, at block 42, the system determines that the patient has genetic findings for a mutation in the CMT1B gene for Charcot-Marie-Tooth disease. The CMT1B is located near the Factor V gene and is a linked gene. Block 44 is bypassed. At block 46, the system determines the traversal pattern for the Factor V gene is autosomal. At block 50, the system determines the family members of the patient within the traversal pattern. At block 52 determines that the patient's mother has a mutated Factor V gene. At block 54, the system determines that the patient's mother has Charcot-Marie-Tooth disease. At block 56, the system utilizes the patient's genetic findings for the CMT1B gene, the mother's genetic findings for the mutated Factor V gene and the mother's phenotypic information for Charcot-Marie-Tooth disease to calculate an inferred result by performing linkage analysis. The system infers that there is a very strong likelihood that the patient has a mutated Factor V gene and is at significant risk of thrombosis if she began estrogen therapy. At block 58 the system informs the gynecologist of the inferred result by sending a pop-up warning.

In another aspect of the invention, the system may determine the risks associated with a specific genetic test result input. For example, genetic findings for one or more family members of a patient may be input. Next, the system determines that few risks are associated with genetic findings for the one or more family members. For example, the system could add a comment to an integrated electronic medical record that no risks were determined for the genetic findings of the patient's family members. Next, the user could be provided with interpretation of the genetic findings. In this case, the user would be provided with an indication that the genetic findings were not associated with any known risks.

Conversely, if genetic risks are known for the relevant genetic findings, a list of potential risks is generated. From this list, a list of agents or events that are associated with the mutation indicated by the genetic test result is generated. Further, the system may determine that the patient has been exposed to the agent or events or may prospectively be exposed to the agent or events. If the patient has been exposed to the agent, the system generates an automated clinical response associated with the high risk. This response may include suspension or cancellation of the order, placing an alternative order, paging the ordering clinician, ordering follow-up tests, or scheduling counseling for the patient. Once all of the agents or events are considered, the user is provided with an automated interpretation of the results. In this case, the interpretation would indicate to the user that certain clinical agents or events should be avoided due to the genetic predisposition to an atypical clinical reaction or that the patient should be tested for the specific gene.

In another embodiment, the completion of a genetic test result for a patient may be used to trigger automated updates to the medical records of family members of the patient. In this embodiment, the patient records of the family members are updated to reflect the probability of the family member sharing the same genetic findings as the patient. In this embodiment, the system would use the genetic findings of the patient along with genetic findings of any others within the family to infer genetic findings for the family member.

Since the system may be integrated with architectures spanning the healthcare organization, the system will operate to manage the risk associated with clinical agents without creating inefficiencies. The system and method of the present invention seamlessly integrates complex genetic information and unchanging genetic information into an overall healthcare system. The invention makes genetics-based logic widely available for use, intended or not, by the non-expert in genetics. This invention adds value to clinical information systems by maximizing the utility of genetic findings. By integrating unchanging hereditary information with newfound knowledge associating this information to certain clinical agents and events, the system will allow the caregiver to appreciate the risks that are not readily apparent from the symptoms of the patient or associated with the particular agent.

Moreover, in the preferred embodiment, the system and method is implemented into a comprehensive automated healthcare system within the context of existing storage media and clinical processes. As mentioned above, the demographic information, familial genetic information and individualized genetic information may be stored in an electronic medical record.

As mentioned at the outset, consideration of the hereditary genetic information may be incorporated in the physician's standard of care, as the implications of the information become widely known. Absent the system and method of the present invention, it would be burdensome and inefficient for non-expert physicians to consider this important genetic information. The inclusion of this information in the electronic medical record or other permanent data structure allows physicians to make decisions based on the latest understandings of genetic information by accessing the updated databases.

Although the invention has been described with reference to the preferred embodiment illustrated in the attached drawing figures, it is noted that substitutions may be made and equivalents employed herein without departing form the scope of the invention as recited in the claims. For example, additional steps may be added and steps omitted without departing from the scope of the invention.

The invention claimed is:

1. A method, implemented by a server, for determining and presenting the likelihood a person has a mutated form of a gene, the method comprising:

receiving an electronic order from a clinician for at least one clinical agent for a person;

in response to receiving the electronic order for the at least one clinical agent, searching a table to determine whether the at least one clinical agent is associated with a gene, the table listing a plurality of genes associated with a plurality of clinical agents and clinical events;

upon searching the table, querying a first database to determine whether the person has one or more genetic test results for the gene determined to be associated with the at least one clinical agent;

when the first database indicates that the person does not have the one or more genetic test results for the gene, identifying an appropriate traversal pattern of the gene within a family of the person identified, wherein the traversal pattern of the gene is identified by a process comprising:

(a) accessing an inference table that associates genes with a plurality of modes of inheritance;

(b) querying the inference table with the gene to select a mode of inheritance that corresponds with the gene; and (c) using the selected mode of inheritance to determine the traversal pattern of the gene within the person's family;

identifying at least one family member within the identified traversal pattern of the person's family for inspection;

querying a second database to determine whether at least one identified family member of the person within the traversal pattern has one or more genetic test results related to the gene;

when the at least one identified family member has the one or more genetic test results for the gene, utilizing the one or more genetic test results to automatically calculate a likelihood the person exhibits a mutated form of the gene; and presenting the calculated likelihood the person has a mutated form of the gene to the clinician.

2. The method of claim 1, wherein the second database comprises an electronic medical record for each family member stored within a comprehensive healthcare system.

3. The method of claim 1, further comprising:

when no family member within the identified traversal pattern has the one or more genetic test results for the gene, inquiring whether the at least one identified family member of the person within the traversal pattern has one or more genetic markers related to the gene; and when the at least one identified family member of the person within the traversal pattern has one or more genetic markers related to the gene, performing a haplotype analysis utilizing the one or more genetic markers to predict a likelihood that the person expresses a mutated form of the gene.

4. The method of claim 1, further comprising:

when no family member within the identified traversal pattern has the one or more genetic test results for the gene, determining that the person has one or more genetic findings for one or more linked genes associated with the gene; and utilizing the one or more linked genes of the person to calculate the likelihood the person has a mutated form of the gene.

5. The method of claim 1, further comprising providing one or more non-transitory computer storage media having computer executable instructions to carry out at least one step of the method.

6. The method of claim 1, further comprising:

determining whether the mutated form of the gene is a gene variant indicative of an atypical event.

7. The method of claim 6, wherein if the mutated form of the gene is a gene variant indicative of an atypical event, presenting an alert to a user.

8. The method of claim 1, wherein the mode of inheritance is selected from one of a mitochondrial DNA mode of inheritance, an X-linked mode of inheritance, a Mendelian mode of inheritance, and a Y-linked mode of inheritance.

9. The method of claim 1 wherein said first and second databases are the same database.

10. A computer system for determining and presenting the likelihood a person has a mutated form of a gene, the computer system comprising:

a server configured to execute:

(1) a receiving module for receiving an electronic order for at least one clinical agent for a person from a clinician, wherein the electronic order does not indicate a request to use genetic techniques to characterize the person's response to the at least one clinical agent for the person;

(2) a determining module for:

(a) determining, in response to receiving the electronic order, whether the at least one clinical agent is associated with a gene, and (b) searching an inference table to determine a maximum distance away from the gene to search for genetic findings of linked genes for the person;

(3) a first querying module for querying, in response to the electronic order, a first database to determine if the person has one or more genetic test results for the gene if the at least one clinical agent is associated with one or more genetic test results;

(4) an obtaining module for, when the person does not have the one or more genetic test results for the gene, identifying an appropriate traversal pattern of the gene within a family of the person, wherein the traversal pattern of the gene is identified by a process comprising:

(a) accessing an inference table that associates genes with a plurality of modes of inheritance;

(b) querying the inference table with the gene to select a mode of inheritance that corresponds with the gene;

(c) using the selected mode of inheritance to determine the traversal pattern of the gene within the person's family; and (d) identifying at least one family member related to the person within the identified traversal pattern of the person's family for inspection;

(5) a second querying module for querying a second database to determine whether at least one identified family member of the person within the traversal pattern has one or more genetic test results for the gene;

(6) a utilizing module for utilizing the one or more genetic test results of the at least one family member to automatically calculate a likelihood the person has a mutated form of the gene if at least one of the family members has genetic test results for the gene; and (7) a presenting module for presenting the calculated likelihood the person has a mutated form of the gene to the clinician without solicitation from the clinician for the calculated likelihood.

11. The system of claim 10, wherein the second database comprises an electronic medical record for each family member stored within a comprehensive healthcare system.

12. The system of claim 10, wherein the second querying module determines the mode of inheritance has one or more genetic markers related to the gene.

13. The system of claim 12, wherein the utilizing module utilizing the one or more genetic markers of at least one family member of the person to calculate the likelihood the person has a mutated form of the gene.

14. The system of claim 10, wherein the first database comprises an electronic medical record for the person.

15. The system of claim 10, further comprising:

a determining module for determining whether the mutated form of the gene is a gene variant indicative of an atypical event.

16. The system of claim 15, wherein if the mutated form of the gene is a gene variant indicative of an atypical event, the presenting module presents an alert to a user.

17. The system of claim 10, wherein the mode of inheritance is selected from one of a mitochondrial DNA mode of inheritance, an X-linked mode of inheritance, a Mendelian mode of inheritance, and a Y-linked mode of inheritance.

18. A method, implemented by a server, for determining and presenting the likelihood a person has a mutated form of a gene, the method comprising:

receiving from a clinician an order for a medication for a person, wherein the order does not indicate a request to use genetic techniques to characterize the person's response to the medication;

in response to receiving the clinician order for medication, determining whether the order for medication is associated with a gene;

querying a first database to determine if the person has one or more genetic test results for the gene;

when the first database indicates that the person does not have the one or more genetic test results for the gene, identifying an appropriate traversal pattern of the gene within a family of the person identified, wherein the traversal pattern of the gene is identified by a process comprising:

(a) accessing an inference table that associates genes with a plurality of modes of inheritance;

(b) querying the inference table with the gene to select a mode of inheritance that corresponds with the gene; and (c) using the selected mode of inheritance to determine the traversal pattern of the gene within the person's family;

identifying at least one family member within the identified traversal pattern of the person's family for inspection;

querying a second database to determine whether at least one identified family member of the person within the traversal pattern has one or more genetic test results related to the gene;

when the at least one identified family member has the one or more genetic test results for the gene, utilizing the one or more genetic test results to automatically calculate a likelihood the person exhibits a mutated form of the; and when the at least one identified family member does not have the one or more genetic test results for the gene, automatically determining whether inferred results are allowed for the gene;

when inferred results are allowed, automatically calculating an inferred finding that the person has a mutated form of the gene based, in part, on one or more genetic findings expressed by the person, wherein the one or more genetic findings include markers linked to the gene; and outputting the inferred finding to a display for presentation in a user-readable format within a graphical user interface (GUI).

19. The method of claim 18, further comprising one or more non-transitory computer storage media having computer executable instructons to carry out at least one step of the method.

20. The method of claim 18, further comprising:
determining whether the mutated form of the gene is a gene variant indicative of an atypical event.

21. The method of claim 20, wherein if the mutated form of the gene is a gene variant indicative of an atypical event, presenting an alert to a user.

* * * * *